(12) United States Patent
Otsubo

(10) Patent No.: US 7,901,391 B2
(45) Date of Patent: Mar. 8, 2011

(54) DISPOSABLE PANTS TYPE WEARING ARTICLE

(75) Inventor: Toshifumi Otsubo, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/843,489

(22) Filed: Aug. 22, 2007

(65) Prior Publication Data

US 2008/0051755 A1   Feb. 28, 2008

(30) Foreign Application Priority Data

Aug. 23, 2006   (JP) ................................ 2006-227054

(51) Int. Cl.
*A61F 13/20* (2006.01)

(52) U.S. Cl. .................... 604/385.27; 604/396

(58) Field of Classification Search ............ 604/385.01, 604/385.16, 396

See application file for complete search history.

(56) References Cited

U.S. PATENT DOCUMENTS 6,491,676 B1   12/2002   Suzuki et al.
7,160,282 B2 *   1/2007   Sayama ................... 604/385.28

FOREIGN PATENT DOCUMENTS

JP   03-176052 A   7/1991
JP   3401627 B2   2/2003
WO   2006/093439   *   9/2006

* cited by examiner

*Primary Examiner* — Michele Kidwell
(74) *Attorney, Agent, or Firm* — Lowe, Hauptman, Ham & Berner, LLP

(57) ABSTRACT

A disposable pants type wearing article includes a chassis folded in two halves along a folding guide extending in a transverse direction and these respective halves of the chassis are joined to each other along lateral edges thereof to form the article. Leg openings are defined by upper and lower leg opening edges formed by incisions in the chassis so that these upper and lower leg opening edges extending at a level a predetermined dimension above the folding guide. Above the upper leg opening edges, waist elastic members are attached and, below the lower leg opening edges, crotch elastic member are attached to the diaper. Under the contraction of these elastic members, a transverse dimension of the zone in which the waist elastic members are attached to the diaper 1 becomes larger than a transverse dimension of the zone in which the crotch elastic members are attached to the diaper.

13 Claims, 8 Drawing Sheets

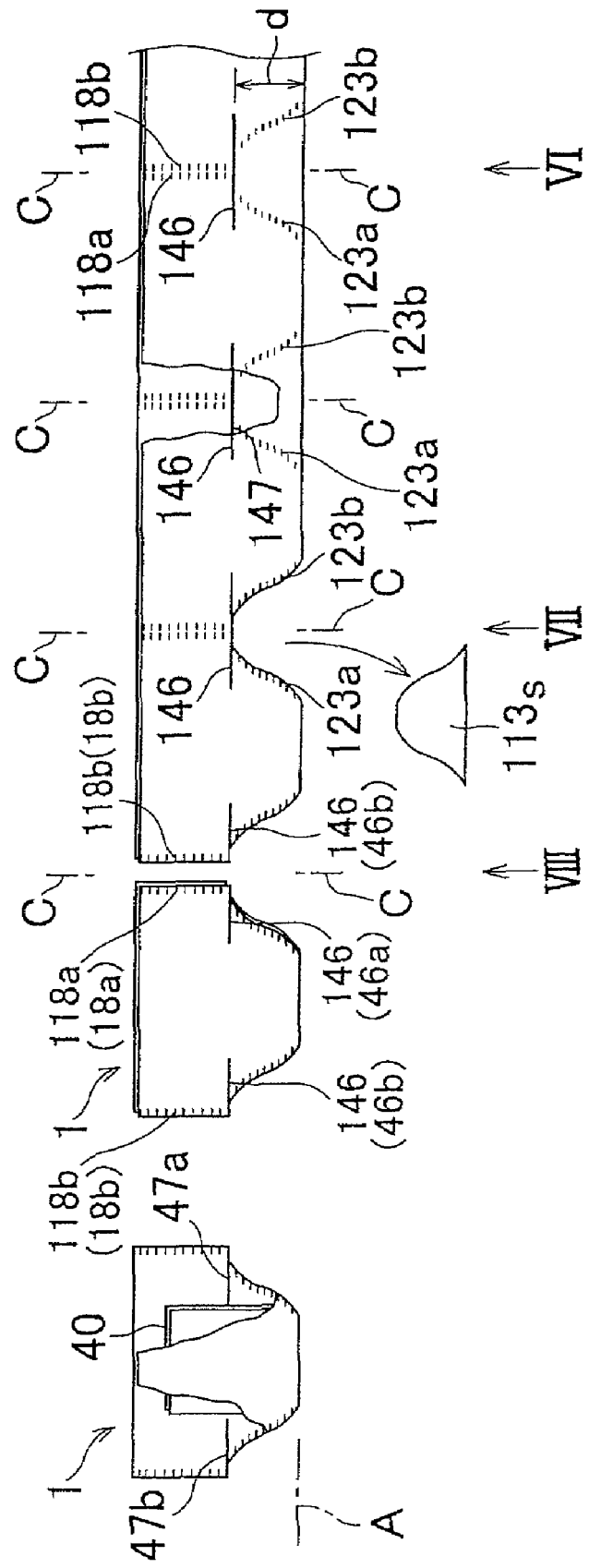

US 7,901,391 B2

DISPOSABLE PANTS TYPE WEARING ARTICLE

RELATED APPLICATIONS

The present application is based on, and claims priority from, Japan Application Number 2006-227054, filed Aug. 23, 2006, the disclosure of which is hereby incorporated by reference herein in its entirety.

BACKGROUND OF THE INVENTION

The present invention relates generally to disposable pants type or pull-on type wearing article having a waist opening and leg openings both adapted to be elastically stretchable and contractible.

Disposable pants type or pull-on type wearing articles having a waist opening as well as leg openings adapted to be elastically stretchable and contractible is well known. For example, Patent Publication No. 3401627 (Reference) discloses such a wearing article of this type under the name of "absorbent article." In this absorbent article, there are provided side panels between opposite lateral edges of a front waist region and opposite lateral margins of a rear waist region. Each of the side panels is made of an elastic sheet material and including an upper zone and a lower zone which are sectionalized by an opening provided in a longitudinally middle zone of the panel so as to serve as a leg opening. The side panels are folded in two inwardly of the wearing article so that, when the wearer's legs are put through the openings of the respective panels, the upper zones are unfolded outward so as to come in contact with the wearer's waist and the lower zones are left folded so as to come in contact with respective inner sides of the wearer's thighs.

In the case of the well known wearing article as has been described above, the side panels prepared separately of the front and rear waist regions must be attached to these waist regions in order to form the leg openings. In addition, to put this wearing article on the wearer's body, the upper zones of the respective folded panels must be unfolded outward with respect to the wearing article while the lower zones must be left folded inward. In this manner, this wearing article may have problems not only in a process of making this article but also in the course of putting the article on the wearer's body.

SUMMARY OF THE INVENTION

It is an object of the present invention to provide a disposable pants type or pull-on type wearing article improved to solve the problems as have been described above.

The object set forth above is achieved, according to the present invention, by an improvement in a disposable pants type wearing article having a transverse direction and a longitudinal direction, upper and lower directions, and a bodyside and an outside opposed to the bodyside, and comprising a chassis contoured by waist opening edges extending in the transverse direction and lateral edges extending in the longitudinal direction, the chassis having halves folded in two along a folding guide extending in the transverse direction with the bodyside inside, the halves of the chassis being joined to each other along the lateral edges to define a front waist region, a rear waist region, a crotch region, a waist opening and a pair of leg openings wherein the waist opening edges and edges of the leg openings are elasticized.

The improvement according to the present invention comprises the following features. The waist opening is defined by the waist opening edges. Each of the leg openings is defined by upper and lower leg opening edges extending in the transverse direction in lateral portions of the front and rear waist regions along vicinities of boundaries of the front and rear waist regions and the crotch region. The chassis is attached in the front and rear waist regions between the waist opening edges and the upper leg opening edges with a plurality of waist elastic members extending in the transverse direction while the chassis is attached in the crotch region between the lower leg opening edges and the folding guide with a plurality of crotch elastic members extending in the transverse direction so that a dimension in the transverse direction of a zone in vicinities of the upper leg opening edges is larger than a dimension in the transverse direction of a zone in vicinities of the lower leg opening edges under contraction of the waist and crotch elastic members.

According to one preferred embodiment of the invention, the crotch region is provided on the bodyside of a middle portion of the crotch region with an absorbent zone extending into the front and rear waist regions and the absorbent zone has a stiffness higher than a stiffness of a portion of the chassis extending in the transverse direction outside the absorbent zone.

According to another preferred embodiment of the invention, portions of the chassis extending outside the absorbent zone as viewed in the transverse direction of the crotch region rise up along lateral edges of the absorbent zone in the longitudinal direction curved in a U-shape, thereby forming leak barriers on both sides of the absorbent zone under contraction of the crotch elastic members.

According to still another preferred embodiment of the invention, the upper and lower leg opening edges extend horizontally in the transverse direction.

According to yet another preferred embodiment of the invention, a dimension of the upper and lower leg opening edges on a side of the front waist region is larger than a dimension of the upper and lower leg opening edges on a side of the rear waist region as viewed in the longitudinal direction of the wearing article.

According to still yet another preferred embodiment of the absorbent zone is defined by an absorbent structure comprising at least an absorbent core and a liquid-pervious inner sheet covering at least the bodyside of the absorbent core.

In the case of the disposable pants type wearing article according to the present invention, the chassis folded in two halves in the longitudinal direction with the bodyside inside and these halves are joined together along lateral edges. The upper and lower leg opening edges in the front waist region extend in the lateral portions thereof while the upper and lower leg opening edges in the rear waist region extend in the lateral portions thereof so as to define the leg openings. Above the upper leg opening edges, the waist elastic members extending in the transverse direction of the wearing article are attached to the chassis and, below the lower leg opening edges, the crotch elastic members extending in the transverse direction of the wearing article are attached to the chassis. The dimension in the transverse direction of the zone in vicinities of the upper leg opening edges is larger than the dimension on the transverse direction of the zone in vicinities of the lower leg opening edges under contraction of the waist and crotch elastic member. Consequently, the chassis forms a large loop immediately above the leg openings and a small loop immediately below the leg openings when the front and rear waist regions are annularly spaced apart from each other in order to wear the article. Differential size of such loops, the leg openings defined between the portion above the upper leg opening edges and the portion below the lower leg opening edges are automatically broadened to facilitate the wearer's legs to be put through the leg openings. Such leg openings can be obtained by the upper and lower leg opening edges which are defined by the incisions made in the chassis. In this way, the wearing article can be made by a simplified process.

According to the embodiment of the invention wherein the crotch region is provided in its middle portion as viewed in the transverse direction with an absorbent zone having a relatively high stiffness, the contraction of the crotch elastic members in the middle portion of the wearing article as viewed in the transverse direction is effectively restrained to prevent this middle portion from getting wrinkles.

According to the embodiment of the invention wherein the chassis rise up along the lateral edges of the absorbent zone and form the leak barriers under contraction of the crotch elastic members, the leg openings can be sufficiently broadened to facilitate the wearer's legs to be put therethrough and, at the same time, it is facilitated to prevent body fluids from leaking sideways in the crotch region.

Advantages achieved by the other embodiments will be apparent from the description of the preferred embodiments given hereunder.

BRIEF DESCRIPTION OF THE DRAWINGS

FIG. 8 is a diagram similar to FIG. 4, illustrating an alternative process for making the diaper.

DETAILED DESCRIPTION OF THE PREFERRED EMBODIMENTS

Details of a disposable pants type or pull-on diaper as an example of a wearing article according to the present invention will be more fully understood from the description given hereunder with reference to the accompanying drawings.

Figure 1:
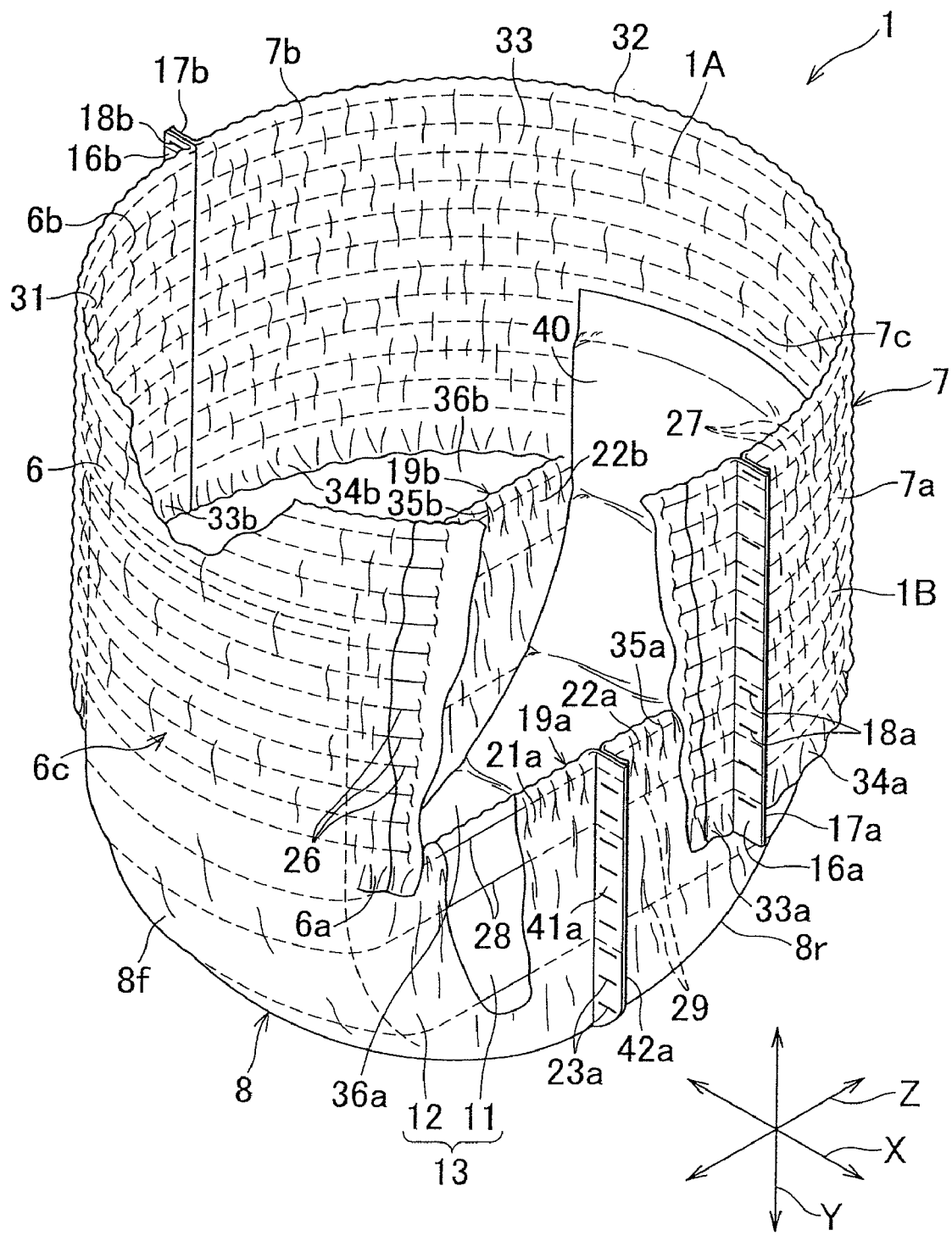
FIG. 1 is a partially cutaway perspective view of a pants type or pull-on type diaper.
Figure 2:
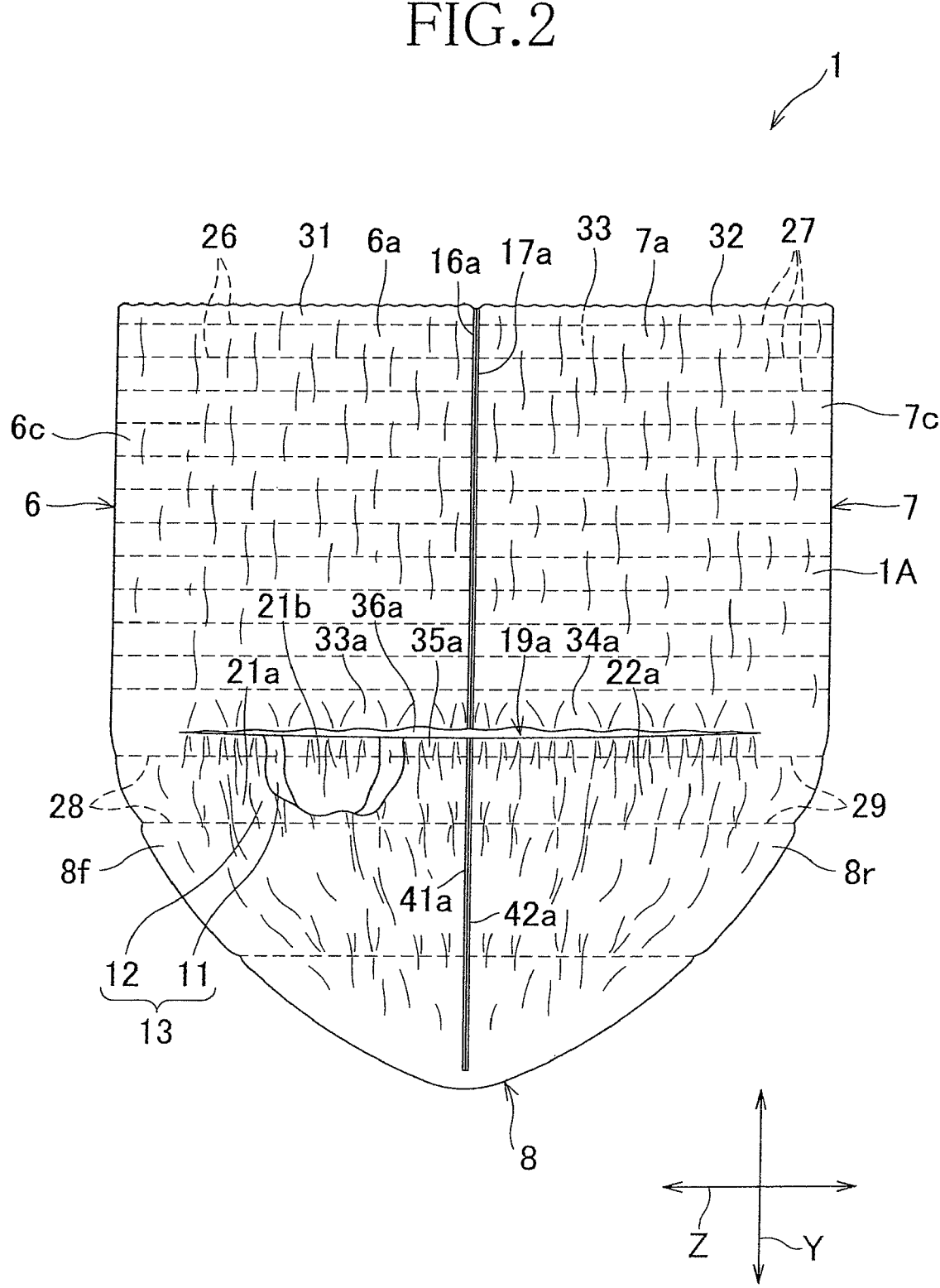
FIG. 2 is a partially cutaway side view of the diaper.

FIG. 1 is a partially cutaway perspective view showing a diaper 1 and FIG. 2 is a partially cutaway side view of the diaper 1 wherein a transverse direction, a longitudinal direction and a back-and-forth direction of the diaper 1 are indicated by arrows X, Y, Z, respectively, which are orthogonal one to another. The transverse direction X corresponds to a width direction of the diaper 1 and therefore will be sometimes referred to also as the width direction X. The longitudinal direction Y corresponds to upper and lower directions or a vertical direction of the diaper 1 and therefore will be sometimes referred to also as the upper and lower directions or the vertical direction Y. The diaper 1 has a front waist region 6, a rear waist region 7 and a crotch region 8 continuous to these waist regions 6, 7 in respective middle portions 6c, 7c thereof as viewed in the width direction X. These front waist region 6, rear waist region 7 and crotch region 8 are formed of a chassis 13 composed of an inner sheet 11 and an outer sheet 12 placed upon and intermittently bonded to each other wherein the front waist region 6 and the rear waist region 7 respectively have lateral portions 6a, 6b and 7a, 7b extending outward from the respective middle portions 6c, 7c in the width direction X (See FIG. 3). The lateral portions 6a, 6b and 7a, 7b respectively have lateral edges 16a, 16b and 17a and 17b wherein the lateral edge 16a is put flat together with the lateral edge 17a while the lateral edge 16b is put flat together with the lateral edge 17b. The lateral edges 16a and 17a are joined to each other at a plurality of sealing spots 18a intermittently arranged in the vertical direction Y and, in the same manner, the lateral edges 16b and 17b are joined to each other at a plurality of sealing spots 18b intermittently arranged in the vertical direction Y. The crotch region 8 has a front half 8f which is continuous to the front waist region 6 in the middle portion 6c thereof, a rear half 8r which is continuous to the rear waist region 7 in the middle portion 7c and leak barriers 19a, 19b formed on both sides of these front half 8f and the rear half 8r. The leak barriers 19a, 19b respectively have front halves 21a, 21b and rear halves 22a, 22b wherein the front half 21a and the rear halves 22a are joined together below the lateral edges 16a, 17b while the front half 21b and the rear half 22b are joined together below the lateral edges 16b, 17b. The front halves 21a, 21b are joined to the rear halves 22a, 22b, respectively, at a plurality of sealing spots 23a, 23b (See FIG. 3) arranged along lateral edges 41a, 41b, 42a, 42b (See FIG. 3) intermittently in the vertical direction. In the front and rear waist regions 6, 7, a plurality of waist elastic members 26, 27 extending in parallel one to another in the width direction, respectively, between the inner sheet 11 and the outer sheet 12 wherein these waist elastic members 26, 27 are attached in a stretched state to at least one of the inner sheet 11 and the outer sheet 12 by means of hot melt adhesives (not shown). In the front half 8f and the rear half 8r of the crotch region 8, a plurality of crotch elastic members 28, 29 exclusively for the crotch region 8 extend in parallel to the waist elastic members 26, 27 wherein these crotch elastic members 28, 29 are attached in a stretched state to at least one of the inner sheet 11 and the outer sheet 12 by means of hot melt adhesives (not shown).

FIG. 1 shows the diaper 1 with the waist elastic members 26, 27 as well as with the crotch elastic members 28, 29 in a state of contraction and the front and rear waist regions 6, 7 annularly spaced from each other. In this state, an upper edge 31 of the middle portion 6c and the lateral portions 6a, 6b of the front waist region 6 (hereinafter referred to as "waist opening edge 31") cooperate with an upper edge 32 of the middle portion 7c and the lateral portions 7a, 7b of the rear waist region 7 (hereinafter referred to as "waist opening edge 32") to define a waist opening 33. The lateral portions 6a, 6b and 7a, 7b of the front and rear waist regions 6, 7 have lower edges 33a, 33b (hereinafter referred to as "upper leg opening edges 33a, 33b") extending parallel to the waist opening edge 31 and lower edges 34a, 34b (hereinafter referred to as "upper leg opening edges 34a, 34b") extending parallel to the waist opening edge 32, respectively. The leak barriers 19a, 19b respectively have upper edges 35a, 35b (hereinafter lower leg opening edges 35a, 35b), respectively, extending in the back-and-forth direction Z substantially in a horizontal position as viewed in FIG. 2 so that a pair of leg openings 36a, 36b is respectively defined between the upper leg opening edges 33a, 34a and the lower leg opening 35a and between the upper leg opening edges 33b, 34b and the lower leg opening 35b, respectively. The leak barriers 19a, 19b are illustrated herein to rise upward from a bottom of the diaper 1 and at the same time to extend linearly in the back-and-forth direction Z. The diaper 1 is shown herein to have an absorbent zone 40 defined by an absorbent structure attached to the inner sheet 11 of the chassis 13. The absorbent structure 40 is laid between the leak barriers 19a, 19b in the crotch region 8 and extends into the front and rear waist regions 6, 7. A plurality of gathers seen in the lateral portions 6a, 6b, 7a, 7b and the leak barriers 19a, 19b are due to the contraction of the waist elastic members 26, 27 and the crotch elastic members 28, 29. Gathers are seen also in the middle portions 6c, 7c, the front half 8f and the rear half 8r.

Figure 3:
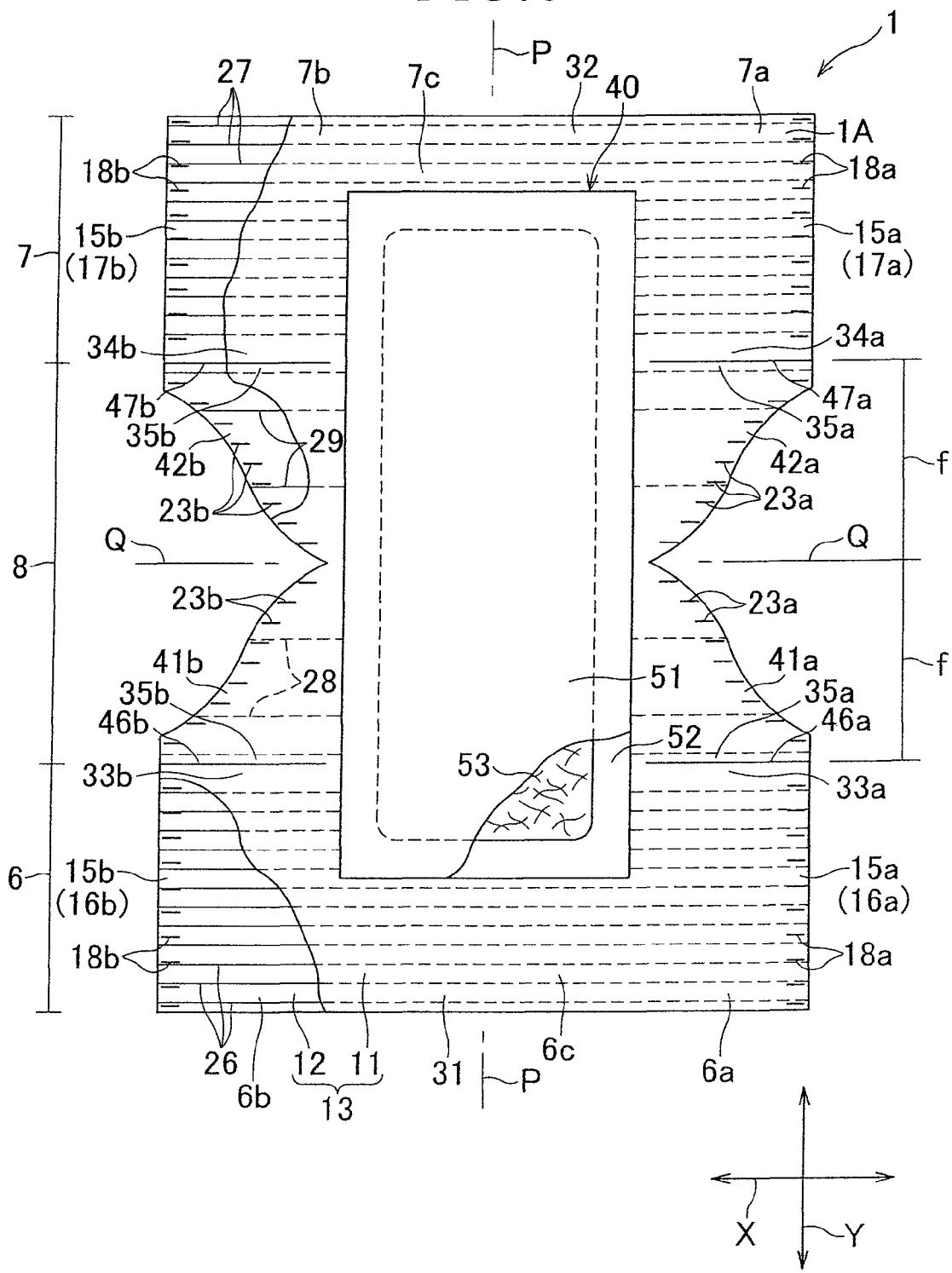
FIG. 3 is a developed plan view of the flattened diaper.

FIG. 3 is a partially cutaway plan view of the diaper 1 after the chassis 13 folded in two and joined together at the sealing spots 18a, 18b, 23a, 23b has been forcibly released at these sealing spots and developed in the width direction X as well as in the back-and-forth direction Z so that the waist elastic members 26, 27 as well as the crotch elastic members 28, 29 are stretched in the width direction X. Referring to FIG. 3, P-P designates a longitudinal center line bisecting a dimension of the diaper 1 in the transverse direction X and Q-Q designates a transverse center line bisecting a dimension of the diaper 1 in the longitudinal direction Y. While the chassis 13 as well as the diaper have a thickness direction which is orthogonal to these two directions X and Y, in addition to these two directions X, Y, this thickness direction is not designated herein by any referential mark. In the state as illustrated in FIG. 3, the waist opening edges 31, 32 shown in FIG. 1 to lie in a line now extend in parallel to each other in the transverse direction X. The lateral edges 16a, 17a lie on a line as viewed in the longitudinal direction Y so as to form one 15a of the lateral edges 15 and the lateral edges 16b, 17b lie on a line as viewed in the longitudinal direction Y so as to form the other 15b of the lateral edges 15. The chassis 13 is notched in a laterally opening V-shape between the lateral edges 16a, 17a and notched in the same manner between the lateral edges 16b, 17b. Lateral edges defining the respective V-shaped notches correspond to the lateral edges 41a, 41b and 42a, 42b of the leak barriers 19a, 19b in FIG. 1. These lateral edges defining these V-shaped notches are in a symmetrical relationship about the longitudinal center line P-P.

Referring to FIG. 3, the chassis 13 in the front waist region 6 is formed at a level spaced apart downward from the transverse center line Q-Q by a predetermined dimension f with a pair of front incisions 46a, 46b horizontally extending from the lateral edges 16a, 16b close to lateral edges of the absorbent structure 40. Also in the rear waist region 7, the chassis 13 is formed at a level spaced apart upward from the transverse center line Q-Q by the predetermined dimension f with a pair of rear incisions 47a, 47b horizontally extending from the lateral edges 17a, 17b close to the lateral edges of the absorbent structure 40. These front incisions 46a, 46b and the rear incisions 47a, 47b made in the chassis 13 in form of slits which are in a symmetrical relationship about the transverse center line Q-Q so far as this embodiment is concerned.

The waist elastic members 26, 27 and the crotch elastic members 28, 29 horizontally extend in parallel to the transverse center line Q-Q. The waist elastic members 26, 27 extend between the lateral margins 16a, 16b of the front waist region 6 and extend between the lateral edges 17a, 17b of the rear waist region 7, respectively. The crotch elastic members 28, 29 extend between the lateral edges 41b and between the lateral edges 42a, 42b, respectively.

The absorbent structure 40 is attached to the inner sheet 11 of the chassis 13 so that a longitudinal center line of the absorbent structure 40 may be defined by the longitudinal center line P-P. The absorbent structure 40 comprises a liquid-pervious bodyside liner 51, a liquid-impervious backsheet 52 and a liquid-absorbent core 53 sandwiched between these two liner and backsheet 51, 52. The bodyside liner 51 and the backsheet 52 extend outward beyond a peripheral edge of the core 53 and portions of these liner and backsheet 51, 52 extending outward beyond the peripheral edge of the core 53 are put flat and bonded together by means of adhesions or sealings. The backsheet 52 is bonded to the inner sheet 11 of the chassis 13 by means of adhesions or sealings. Stock materials for the inner sheet 11 and the outer sheet 12 of the chassis 13 may be selected from the group consisting of liquid-pervious or liquid-impervious nonwoven fabrics or woven fabrics and plastic films. The core 53 may be formed, for example, by fluff pulp fibers or mixture of fluff pulp fibers and super-absorbent polymer particles wrapped with a liquid absorbent and spreadable sheet such as tissue papers or non-woven fabrics.

The chassis 13 constructed and developed as shown in FIG. 3 may be folded upward in the longitudinal direction along the transverse center line Q-Q serving as a folding guide with the inner sheet 11 inside so that the front and rear waist regions 6, 7 are put flat together. Then the lateral edges 16a, 16b of the front waist region 6 are joined to the lateral edges 17a, 17b of the rear waist region 7 at the sealing spots 18a, 18b, respectively. In the crotch region 8 also, the lateral edges 41a, 41b are joined to the lateral edges 42a, 42b at the sealing spots 23a, 23b, respectively. The incisions 46a, 46b, 47a, 47b made in the chassis 13 serve to define the upper leg opening edges 33a, 33b, 34a, 34b and the lower leg opening edges 35a, 35b, respectively. Additionally, in the diaper 1 shown in FIG. 3, the waist elastic members 26, 27 and the crotch elastic members 28, 29 are adjusted so that respective widths of the front and rear waist regions 6, 7 as measured between the sealing spots 18a and the sealing spots 18b becomes larger than a width of the crotch region 8 as measured between the sealing spots 23a, 23b in vicinities of the incisions 46a, 46b, 47a, 47b. To achieve this, for example, the crotch elastic members 28, 29 may be attached to the chassis 13 so as to have a tensile strength higher than a tensile strength of the waist elastic members 26, 27 so far as the rubber strings of the same type are used as the waist elastic members 26, 27 and the crotch elastic members 28, 29.

Referring again to FIG. 1, the contraction of these elastic members 26, 27, 28, 29 causes a dimensional relationship of the respective regions in the diaper 1 in such a manner that a summed-up length of the upper leg opening edges 33a, 34a becomes longer than a length of the lower leg opening edge 35a and a summed-up length of the upper leg opening edges 33b, 34b becomes longer than a length of the lower leg opening edge 35b. With the waist elastic members 28, 29 maintained in a state of contraction, the front and rear waist regions 6, 7 may be annularly spaced apart from each other and the absorbent structure 40 may be deformed in a U-shape to cause the portions of the chassis 13 defining the leak barriers 19a, 19b in the crotch region 8 to raise up themselves along the opposite lateral edges of the absorbent structure 40 and to extend rectilinearly in the back-and-forth direction Z. Thereupon, the leg openings 36a, 36b are fully broadened. It should be understood here that the absorbent structure 40 has a sufficiently high stiffness to be substantially free from a possibility that the absorbent structure 40 might be significantly contracted or bent in the width direction X under the contractile force of the elastic members 26, 27, 28, 29. Consequently, the contraction of the elastic members 26, 27 is expressed preliminarily in contraction of the chassis 13 occurring in the lateral portions 6a, 6b, 7a, 7b of the front and rear waist regions 6, 7 while the contraction of the elastic members 28, 29 is expressed preliminarily in contraction of the chassis 13 occurring in the portions thereof defining the leak barriers 19a, 19b in the crotch region 8. Apparently, the width of the diaper 1 in vicinities of the incisions 46a, 46b, 47a, 47b is relatively large immediately above these incisions 46a, 46b, 47a, 47b and relatively small immediately below these incisions 46a, 46b, 47a, 47b.

Figure 4:
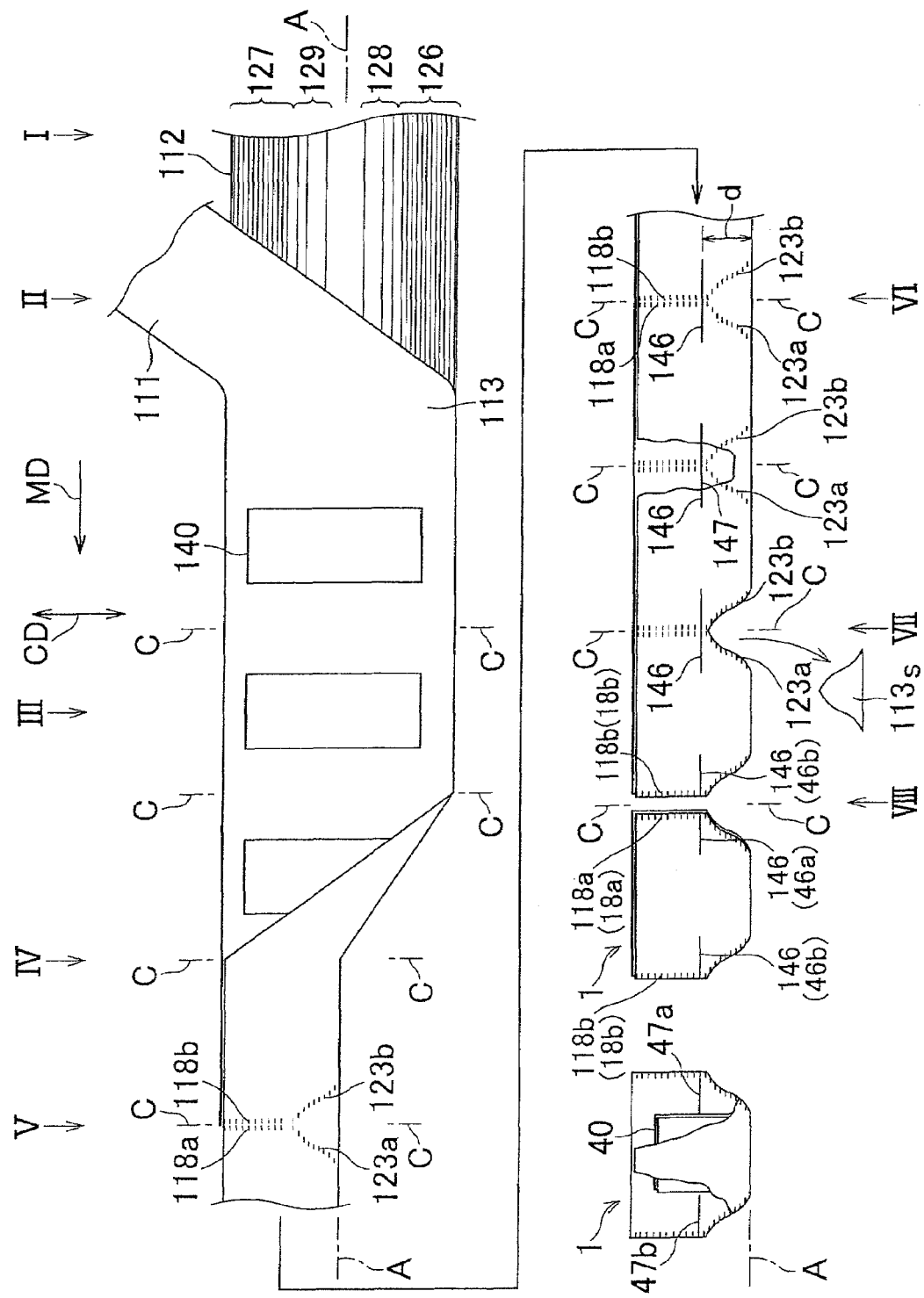
FIG. 4 is a diagram partially illustrating a process for making the diaper.

FIG. 4 is a diagram partially illustrating a process for making the diaper 1 of FIG. 1. In FIG. 4, a machine direction and a cross direction which is orthogonal to the machine direction are indicated by MD and CD, respectively.

In a step I of the process illustrated in FIG. 4, a continuous web 112 destined to become the outer sheet 12 is fed in the machine direction MD. The continuous web 112 destined to become the outer sheet 12 has previously been provided with first through fourth elastic members 126 through 129 continuously extending in the machine direction MD and attached in a stretched state thereto. The first and second elastic members 126, 127 are destined to become the waist elastic members 26, 27 and the third and fourth elastic members 128, 129 are destined to become the crotch elastic members 28, 29. The third and fourth elastic members 128, 129 are selected so as to contract a continuous web 113 destined to become the chassis 13 as will be described later in more detail.

In a step II, a continuous web 111 destined to become the inner sheet 11 is fed in the machine direction MD and bonded to the continuous web 112 destined to become the outer sheet 12 by means of adhesions or sealing techniques to obtain the continuous web 113 destined to become the chassis 13 comprising the first through fourth elastic members 126 through 129 sandwiched between the continuous webs 111, 112.

In a step III, absorbent structures 140 are attached to the continuous web 111 destined to become the inner sheet 11 at a regular interval in the machine direction MD. Chain line C-C passing through a middle point (not shown) between each pair of the adjacent absorbent structures 140, 140 is the line allocated for cutting of the continuous web 113 in a later step.

In a step IV, the continuous web 113 destined to become the chassis 13 is folded back on itself along a center line A-A bisecting this continuous web 113 in the cross direction CD.

In a step V, a pair of sealing spot assemblies arranged on both sides of the line C-C allocated for cutting so as to extend in parallel to and symmetrical about the line C-C and a pair of sealing spot assemblies 123a, 123b extending so as to intersect with the line C-C are formed and respective halves of the continuous web 113 destined to become the chassis 13 folded back on each other in the precedent step are bonded to each other.

In a step VI, the continuous web 113 destined to become the chassis 13 is formed with combined incisions 146, 147. These combined incisions 146, 147 are made through the continuous web 113 destined to become the chassis 13 folded back on itself in its thickness direction. A length of the combined incisions 146, 147 as measured in the machine direction MD is equal to a distance d from the center line A-A to the combined incisions 146, 147 as measured in the cross direction CD. The combined incisions 146, 147 extend between each pair of the adjacent absorbent structure 140, 140.

In a step VII, a segment 113s defined below the sealing spot assemblies 123a and 123b is cut away from the continuous web 113 destined to become the chassis 13.

In a step VIII, the continuous web 113 destined to become the chassis 13 is successively cut along the respective lines C-C allocated for cutting to obtain the individual diapers 1.

Materials used in the steps I through VIII correspond to the components or the members in the individual diaper 1 in the manner as will be described. The continuous web 111 and the continuous web 112 correspond to the inner sheet 11 and the outer sheet 12, respectively. The elastic members 126, 127, 128, 129 correspond to the waist elastic members 26, 27 and the crotch elastic members 28, 29, respectively. The absorbent structure 140 corresponds to the absorbent structure 40. The sealing spot assemblies 118a, 118b, 123a, 123b formed in the associated steps correspond to the sealing spots 18a, 18b, 23a, 23b. The combined incision 146 corresponds to the incisions 46a, 46b and the combined incision 147 corresponds to the incisions 47a, 47b. These incisions 46a, 46b, 47a, 47b cooperate one with another to define the leg openings 36a, 36b of the diaper 1.

The individual diaper 1 illustrated by FIG. 4 is similar to the diaper 1 of FIG. 1 except that the waist elastic members 26, 27 as well as the crotch elastic members 28, 29 are illustrated by FIG. 4 to be maintained stretched in the machine direction MD. These elastic members 26, 27, 28, 29 contract as the diaper 1 is free. Upon contraction, a width of the portions of the chassis 13 including the waist elastic members 26, 27 become larger than a width of the portions of the chassis 13 including the crotch elastic members 28, 29. In a typical example of the diaper 1 shown in FIG. 1, the leg opening edges 35a, 35b of the leak barriers 19a, 19b, respectively, in the crotch region 8 more remarkably contract in the machine direction MD in FIG. 4, i.e., in the width direction X of the diaper 1 than the lateral portions 6a, 6b, 7a, 7b of the front and rear waist regions 6, 7. When the elastic members 26, 27, 28, 29 of the diaper 1 contract and the waist opening 33 is annularly broadened as seen in FIGS. 1 and 2, as has previously been described, a length of the lower leg opening edge 35a defining upper end of the leak barrier 19a apparently becomes shorter than a summed-up length of the upper leg opening edge 33a, 34a defining lower edges of the front and rear waist regions 6, 7, respectively, while a length of the lower leg opening edge 35b becomes apparent shorter than a summed-up length of the upper opening edges 33b, 34b. Consequently, the leg openings 36a, 36b are automatically broadened to facilitate the wearer's legs to be put through the leg openings 36a, 36b. The waist elastic members 26, 27 extending in the vicinity of the leg openings 36a, 36b provide for elastically close contact with the outer sides of the respective thighs while the crotch elastic members 28, 29 provide for elastically close contact with the inner sides of the respective thighs.

As will be apparent from the process illustrated by FIG. 4, the leg openings 36a, 36b are easily obtained by making combined incisions 146, 147 between the elastic members 126 and 128 so as to extend in parallel to each other in the machine direction MD as well as between the elastic members 127 and 129 so as to extend in parallel to each other in the machine direction MD. Accordingly, even when it is intended to make the diaper 1 by feeding the continuous web 113 destined to become the chassis 13 in the machine direction MD, it is easy to form the elastic leg openings and there is no problem that the step of forming the elastic leg openings might become a rate-controlling step.

Figure 5:
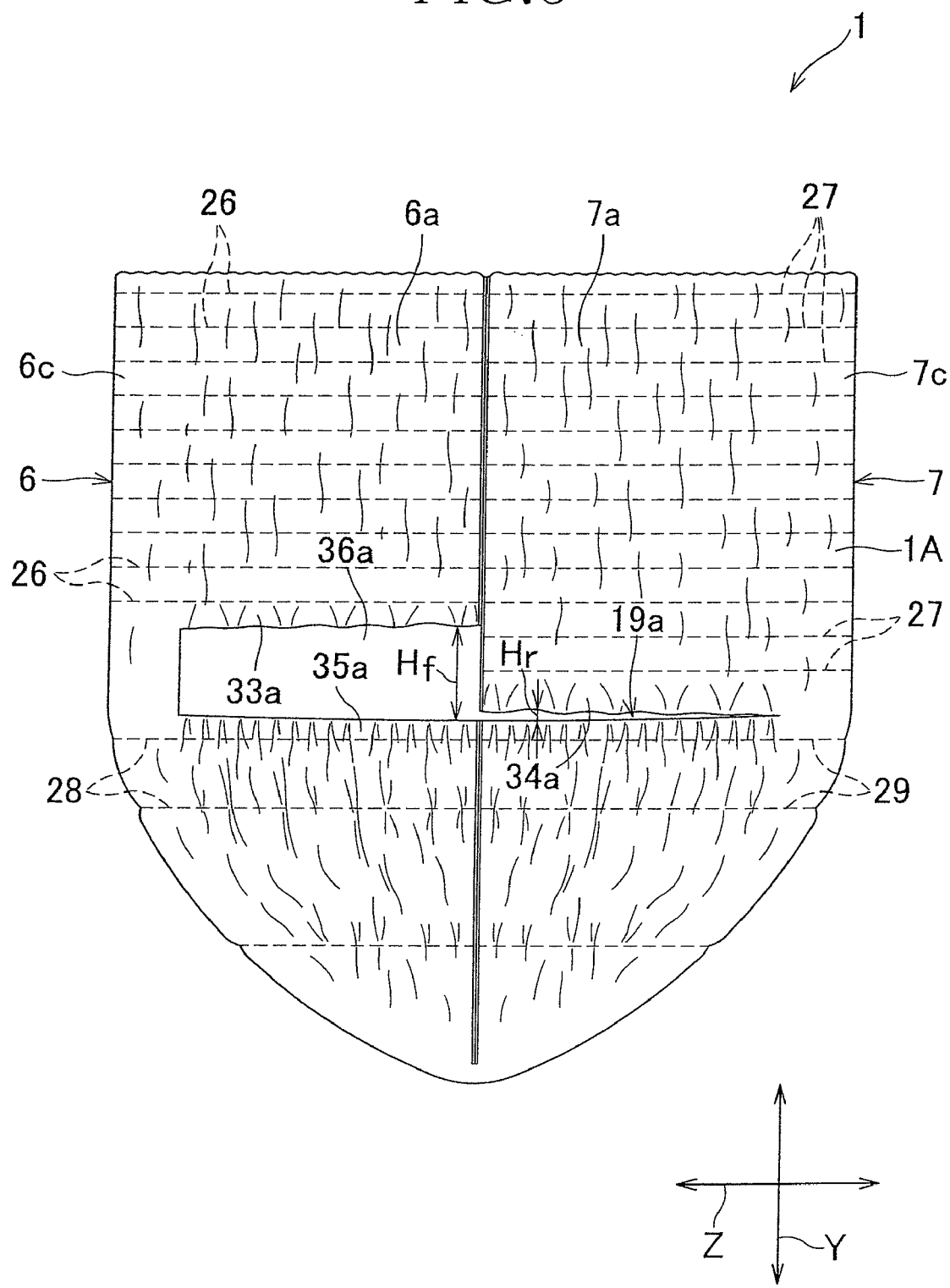
FIG. 5 is a view similar to FIG. 2, showing a preferred embodiment of the invention.

FIG. 5 is a view similar to FIG. 2, showing one preferred embodiment of the invention. The diaper 1 of FIG. 5 has a pair of leg openings configured in a manner different from the manner in which the leg openings 36a, 36b of the diaper 1 shown in FIG. 2. Specifically, in the leg opening 36a shown in FIG. 5, a front dimension $H_f$ between the upper leg opening edge 33a and the lower leg opening edge 35a as measured in the longitudinal direction Y is selected to be larger than a rear dimension $H_r$ between the upper opening edge 34a and the lower opening edge 35a as measured in the longitudinal direction Y. In the case of a baby diaper 1, for example, the front dimension $H_f$ is preferably selected to be in a range of 5 to 70 mm, the rear dimension $H_r$ is preferably selected to be in a range of 0 to 20 mm and a difference between the dimension $H_f$ and the dimension $H_r$ is preferably as small as possible. The description as used herein "dimension $H_r$ of 0 mm"

means that the upper leg opening edge 34a and the lower leg opening edge 35a are defined by making an incision in the rear waist region 7 just like the case of FIG. 2. Peripheral edge of the leg opening 36a is made elasticized by the presence of the front waist elastic member 26 horizontally provided along the upper leg opening edge 33a, the rear waist elastic member 27 horizontally provided along the upper leg opening edge 34a and the crotch elastic members 28, 29 horizontally provided along the lower leg opening edge 35a. The diaper 1 of FIG. 5 is symmetrical about the longitudinal center line P just like the case of the diaper 1 shown in FIGS. 1 through 3. The other leg opening not shown also is symmetrical to the leg opening 19a about the longitudinal center line P-P. In such diaper 1 of FIG. 5, an area of the wearer's body covered with the lateral portions 6a, 6b of the front waist region 6 (See FIG. 3) is reduced as shown while an area of the wearer's body covered with the lateral portions 7a, 7b of the rear waist region 7 is enlarged as shown to improve a feeling to wear the diaper 1 of FIG. 3.

Figure 6:
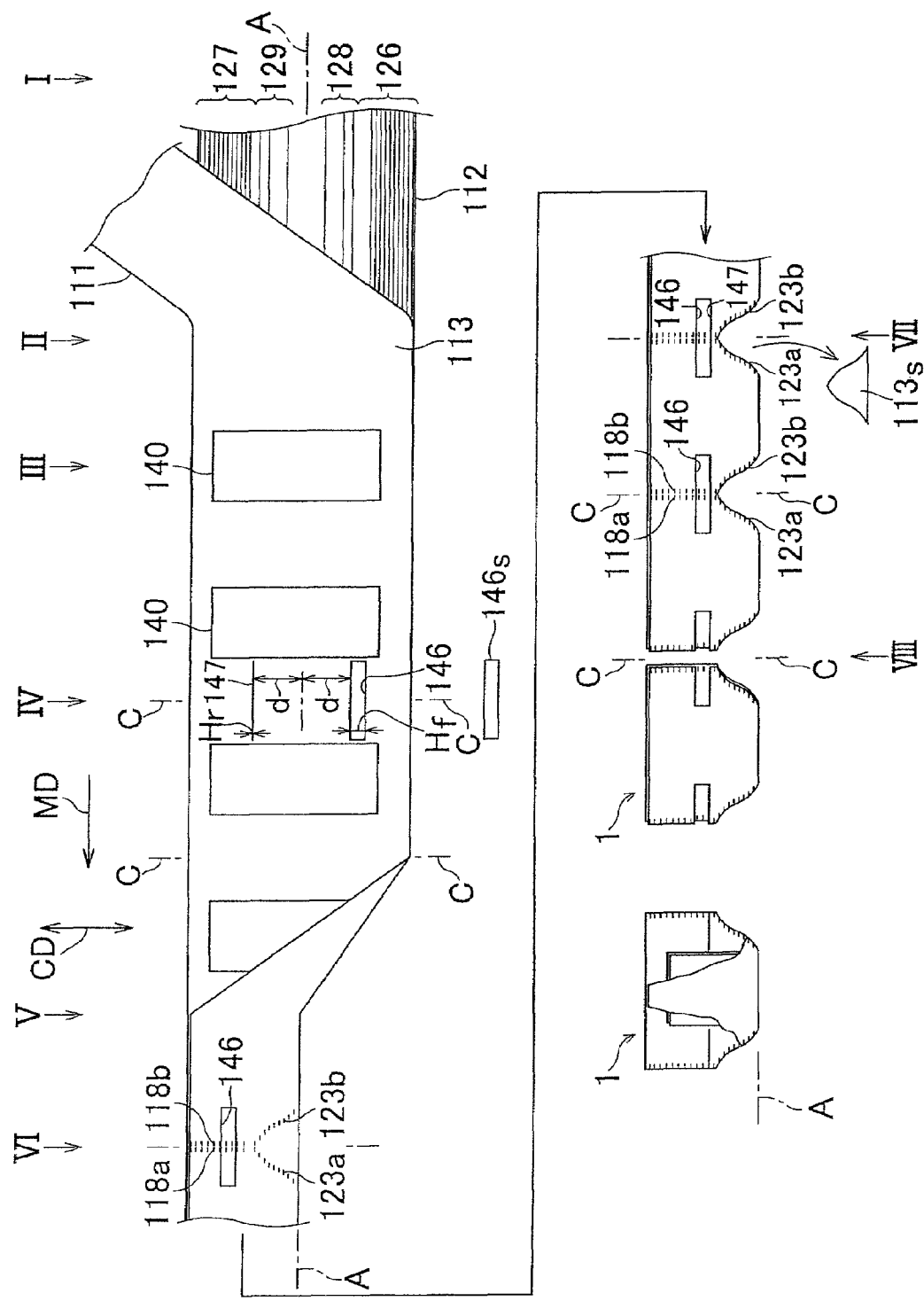
FIG. 6 is a diagram partially illustrating a process for making the diaper of FIG. 5.

FIG. 6 is a diagram similar to FIG. 4, illustrating a process for making the diaper 1 of FIG. 5.

In a step I of the process illustrated by FIG. 6, a continuous web 112 destined to become the outer sheet 12 is fed in the mechanical direction MD. The continuous web 112 destined to become the outer sheet 12 has previously been provided with a plurality of elastic members, i.e., first through fourth elastic members 126 through 129 attached in a stretched state thereto. While the second through fourth elastic members 127 through 129 are similar to those in FIG. 4, the first elastic member 126 is distinguished from the first elastic member 126 in FIG. 4 in the number of rubber strings and/or placement with respect to the continuous web 112 destined to become the outer sheet 12 in order to prevent this first elastic member 126 from overlapping the incision 146 as will be described later more in detail.

Steps II and III are similar to those in FIG. 4 and the absorbent structures 140 are successively attached to the continuous web 113 destined to become the chassis 13 obtained in the step II.

In a step IV, the continuous web 113 destined to become the chassis 13 is formed with first and second composite incisions 146, 147 extending in the machine direction MD so as to intersect with the line allocated for cutting C-C. The first incision 146 extends in the machine direction MD between each pair of the adjacent absorbent structures 140, 140 at a distance d from the center line A-A in the cross direction CD and is formed by cutting away the continuous web 113 so that the first incision 146 may have a width corresponding to the dimension $H_f$ (See FIG. 5) as measured in the cross direction CD. The second composite incision 147 extends in the machine direction MD between each pair of the adjacent absorbent structures 140, 140 at a distance d from the center line A-A in the cross direction CD and is formed by cutting away the continuous web 113 so that the first incision 146 may have a width corresponding to the dimension $H_r$ (See FIG. 5) as measured in the cross direction CD. It should be noted here that the second composite incision 147 is illustrated herein as an incision of which the dimension $H_r$ is substantially 0 mm.

In a step V, the continuous web 113 destined to become the chassis 13 is folded back on itself along the center line A-A with the continuous web 111 destined to become the inner sheet 11 inside.

In a step VI, the sealing spot assemblies 118a, 118b and the sealing spot assemblies 123a, 123b are formed, along which respective halves of the continuous web 113 destined to become the chassis 13 folded back are bonded to each other. These sealing spot assemblies 118a, 118b, 123a, 123b formed to be used for bonding together of the continuous web 113 which have been folded back onto each other may be formed also on the portion of the continuous web 113 exposed through the first composite incision 146.

In a step VII, the portion 113s of the continuous web 113 extending below the sealing spot assemblies 123a, 123b is cut away.

In a step VIII, the continuous web 113 destined to become the chassis 13 is successively cut along the line allocated for cutting C-C to obtain the individual diaper 1 exemplarily shown in FIG. 5.

According to the process illustrated by FIG. 6, the first and second composite incisions 146, 147 are made in the continuous web 113 before the continuous web 113 is folded back on itself, allowing the leg openings 36a, 36b to have differential geometries, respectively, between in the front waist region 6 and in the rear waist region 7, as seen in FIG. 5.

Figure 7:
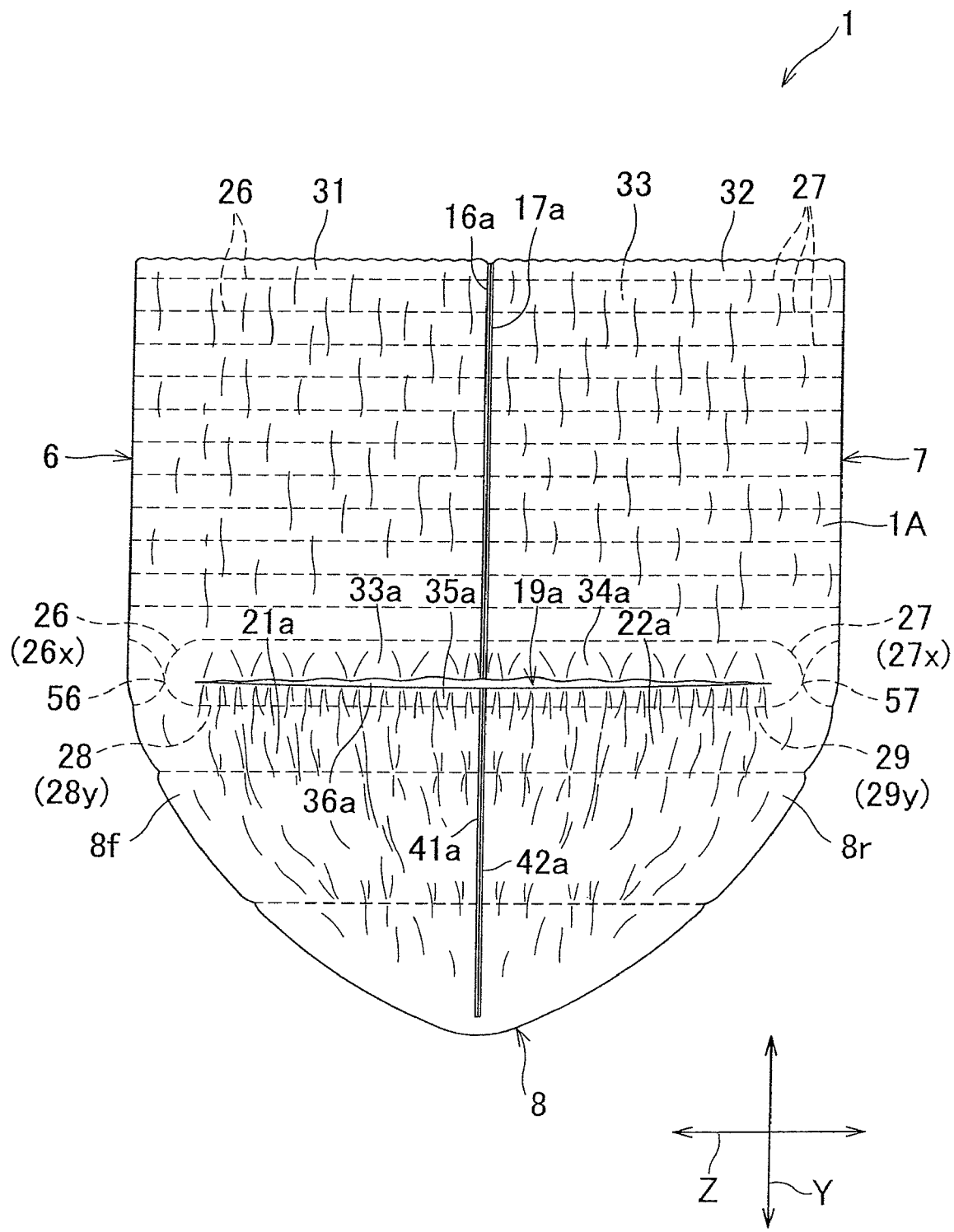
FIG. 7 is a view similar to FIG. 2, showing another preferred embodiment of the invention.

FIG. 7 is a view similar to FIG. 2, showing another preferred embodiment of the invention. In the case of a diaper 1 shown in FIG. 7, an elastic member 26x included in elastic members 26 for the front waist region which is provided immediately above the leg opening 36a intersects with an elastic member 28y included in the elastic members 28 for a front half 8$_f$ of the crotch region at a point 56 on the front half of the leg opening 36a. Similarly, an elastic member 27x included in elastic members 27 for the rear waist region which is provided immediately below the leg opening 36a intersects with an elastic member 29y included in the elastic members 29 for a rear half 8$_r$ of the crotch region at a point 57 on the rear half of the leg opening 36a. Though not illustrated, the elastic member 26x and the elastic member 27x are overlapped on each other or closely adjacent to each other on the lateral margins 16a, 17a so that these two elastic members 26x, 27x are substantially contiguous to each other. Similarly, the elastic member 28y and the elastic member 29y are overlapped on each other or closely adjacent to each other on the lateral margins 41a, 42a so that these two elastic members 28y, 29y are substantially contiguous to each other. In the diaper 1 of FIG. 7, consequentially, these elastic members 26x, 27x, 28y, 29y cooperate together to define a loop-shaped elastic zone adapted to come in close contact with the entire circumference of the wearer's leg put through the associated leg opening 36a. In this way, the diaper 1 assures a high leak barrier effect. The diaper 1 is configured to be symmetrical about the longitudinal center line (See FIG. 3) and therefore the same leak-proof effect can be assured with respect to the other leg opening which is not seen in FIG. 7. It is not essential for the elastic members 26x, 27x, 28y, 29y to extend across the front and rear waist regions 6, 7 as well as across the crotch region 8 so far as these elastic members are present along the peripheral edge of the leg opening 36a.

FIG. 8 is a diagram similar to FIG. 4, illustrating a process for making the diaper 1 of FIG. 7. In a step VI in the process illustrated by FIG. 8, sealing spot assemblies 118a, 118b immediately on both sides of the line C-C allocated for cutting are formed above the composite incisions 146, 147 in the same manner as in the case illustrated by FIG. 4 and, below these composite incisions 146, 147, sealing spot assemblies 123a, 123b largely spaced from each other in the machine direction MD instead of those sealing spot assemblies 123a, 123b in FIG. 4. In a step VII, a segment 113s having a width in the machine direction MD larger than the segment 113s in FIG. 4 is cut away from the continuous web 113. In the diaper 1 obtained by the process illustrated by FIG. 4, the summed-up length of the upper leg opening edges 33a, 34a in the front and rear waist regions 6, 7 defined by the composite incision 146 as well as the summed-up length of the upper leg opening edges 33b, 34b are equal to the lengths of the lower leg opening edges 35a, 35b, respectively, although these lower leg opening edges 35a, 35b appear to be shorter under the effect of the elastic members 26, 27, 28, 29. In the diaper 1 of FIG. 8, on the contrary, the respective length of the lower leg opening edges 35a, 35b is shorter than the summed-up length of the upper leg opening edges 33a, 34a as well as the summed-up length of the upper leg opening edges 33b, 34b not apparently but actually. The respective length of the lower leg opening edges 35a, 35b is further shortened from the length seen in FIG. 8 under the effect of the elastic members 26, 27.

The present invention may be exploited in a manner different from the illustrated embodiments. For example, the absorbent structure 40 attached to the skin-contactable surface of the inner sheet 11 in the illustrated embodiments may be sandwiched between the inner sheet 11 and the outer sheet 12. In this case, a liquid-pervious sheet may be used as the inner sheet 11 and preferably a liquid-impervious sheet is used as the outer sheet 12. Furthermore, the present invention may be exploited as the pants type wearing article using not the absorbent structure 40. Such wearing article is useful as, for example, disposable pants, disposable training pants, pants for incontinent patient. The chassis 13 comprising the inner sheet 11 and the outer sheet 12 in the illustrated embodiments may be formed by the inner sheet 11 or the outer sheet 12 alone. The waist elastic members 26, 27 as well as the crotch elastic members 28, 29 may be partially cut or cut away in the vicinity of the longitudinal center line P-P to assure that the absorbent structure 40 itself as well as the inner and outer sheets 11, 12 covering the absorbent structure 40 is prevented from being formed with gathers as seen in FIG. 1. Without departing from the spirit and the scope of the invention, a plurality of the waist elastic members 26 and 27 may have a tensile strength differing from one another. Similarly, a plurality of the elastic members 28 and 29 for the crotch region 8 also may have a tensile strength differing from one another.

The entire discloses of Japanese Patent Application No. 2006-227054 filed on Aug. 23, 2006 including specification, drawings and abstract are herein incorporated by reference in its entirety.

What is claimed is:

1. A disposable pants type wearing article having an up-and-down direction, a back-and-forth direction, said wearing article comprising:
   a chassis extending in the back-and-forth direction to define a waist opening edge and extending in the up-and-down direction to define lateral edges, said chassis being divided in two halves by a folding guide and said lateral edges in the halves are bonded together,
   said chassis having
   a crotch region extending in the back-and-forth direction from said folding guide which defines a bottom of said chassis;
   front and waist regions extending from said crotch region toward said waist opening edge in the up-and-down direction;
   a pair of leg openings having upper and lower leg opening edges extending in the back-and-forth direction in said front and rear waist regions;
   waist elastic members arranged on said front and rear waist regions and extending in the back-and-forth direction along the waist opening edge; and
   a plurality of crotch elastic members arranged on said crotch region and extending in the back-and-forth direction, wherein a dimension in the back-and-forth direction of said upper leg opening edges is larger than that of said lower leg opening edges under different contractions of said waist and crotch elastic members,
   wherein said lateral edges of the halves of said chassis are directly bonded with each other between the bottom of said chassis and said lower leg opening edges.

2. The wearing article according to claim 1, further comprising an absorbent structure provided on said crotch region, extending and overlaying said front and rear waist regions;
   wherein said absorbent structure has a stiffness higher than a stiffness of the said chassis.

3. The wearing article according to claim 2, wherein said chassis has portions that are located between the bottom of the chassis and the lower leg opening edges and outside said absorbent structure, and extend in the back-and-forth direction,
   wherein said absorbent structure is deformed in a U-shape in the back-and-forth direction, and
   wherein said portions rise up along opposite lateral edges of said U-shaped absorbent structure in the up-and-down direction, and define leak barriers on both sides of said U-shaped absorbent structure under contraction of said crotch elastic members.

4. The wearing article according to claim 1, wherein said upper and lower leg opening edges extend horizontally in the back-and-forth direction.

5. The wearing article according to claim 1, wherein a spacing in the up-and-down direction between said upper and lower leg opening edges in said front waist region is larger than that in said rear waist region.

6. The wearing article according to claim 2, wherein said absorbent structure comprises at least an absorbent core and a liquid-pervious inner sheet covering said absorbent core.

7. The wearing article according to claim 1, wherein said upper leg opening edges and said lower leg opening edges extend in the back-and-forth direction generally straight and parallel to said waist opening edge, respectively.

8. The wearing article according to claim 1, wherein said crotch elastic members extend in the back-and-forth direction between the bottom of said chassis and the lower leg opening edges.

9. The wearing article according to claim 1, wherein said lateral edges of said chassis are directly bonded with each other at sealing spots elongated in the back-and-forth direction so that said waist elastic members and crotch elastic members are stretched in the back-and-forth direction.

10. The wearing article according to claim 5, wherein the spacing in said front waist region is in a range of 5 to 70 mm, and the spacing in said rear waist region is in a range of 0 to 20 mm.

11. The wearing article according to claim 1, wherein said waist elastic members and said crotch elastic members further comprise front and rear waist elastic members and front and rear crotch elastic members, respectively,
   wherein said front waist elastic member intersects with the respective front crotch elastic member; and
   said rear crotch elastic member intersects with the respective rear waist elastic member.

12. The wearing article according to claim 11, wherein said front and rear waist elastic members and said front and rear crotch elastic members cooperate to define elasticized loops surrounding the respective leg openings.

13. The wearing article according to claim 1, wherein said lateral edges of the halves of said chassis are directly bonded with each other at sealing spots arranged intermittently in the up-and-down direction between the bottom of said chassis and said lower leg opening edges.

* * * * *